US006818790B1

(12) United States Patent
Fujita et al.

(10) Patent No.: US 6,818,790 B1
(45) Date of Patent: Nov. 16, 2004

(54) PROCESS FOR PRODUCING MIXED GAS OF LOWER OLEFIN AND LOWER ALIPHATIC CARBOXYLIC ACID, AND PROCESS FOR PRODUCING LOWER ALIPHATIC ESTER USING THE MIXED GAS

(75) Inventors: Ayumu Fujita, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 172 days.

(21) Appl. No.: 09/674,531

(22) PCT Filed: Oct. 4, 2000

(86) PCT No.: PCT/JP00/06924

§ 371 (c)(1),
(2), (4) Date: Nov. 1, 2000

(87) PCT Pub. No.: WO01/25182

PCT Pub. Date: Apr. 12, 2001

Related U.S. Application Data

(60) Provisional application No. 60/162,897, filed on Nov. 1, 1999.

(30) Foreign Application Priority Data

Oct. 5, 1999 (JP) .......................................... 11-284521

(51) Int. Cl.⁷ .............................................. C07C 69/52
(52) U.S. Cl. ........................ 560/205; 562/400; 562/512
(58) Field of Search ................................. 560/205, 129; 562/400, 512

(56) References Cited

U.S. PATENT DOCUMENTS 5,861,530 A * 1/1999 Atkins et al. ................ 560/247

FOREIGN PATENT DOCUMENTS

| EP | 0538826 A2 | * | 4/1993 | |
| EP | 0538826 | * | 4/1993 | |
| EP | 0 538 826 A2 | | 4/1993 | ........... C07C/69/14 |
| GB | 1017604 | * | 12/1961 | |
| JP | 4-139149 | | 5/1992 | |
| JP | 04139149 | * | 5/1992 | |
| JP | 5-170699 | | 7/1993 | |
| JP | 5-294894 | * | 11/1993 | |
| JP | 9-118647 | | 5/1997 | |
| WO | WO 01/25182 | | 4/2001 | |

* cited by examiner

Primary Examiner—Rita Desai
Assistant Examiner—Hector M. Reyes
(74) Attorney, Agent, or Firm—Sughrue Mion, PLLC

(57) ABSTRACT

A process for producing a lower aliphatic ester by catalytically reacting a lower olefin and a lower aliphatic carboxylic acid in a gas phase, where the lower aliphatic carboxylic acid is gasified at a relatively low temperature and thereby a mixed gas of the lower olefin and the lower aliphatic carboxylic acid is produced.

12 Claims, 1 Drawing Sheet

PROCESS FOR PRODUCING MIXED GAS OF LOWER OLEFIN AND LOWER ALIPHATIC CARBOXYLIC ACID, AND PROCESS FOR PRODUCING LOWER ALIPHATIC ESTER USING THE MIXED GAS

CROSS-REFERENCE TO RELATED APPLICATIONS

This application is an application filed under 35 U.S.C. § 111(a) claiming benefit pursuant to 35 U.S.C. § 119(e)(1) of the filing date of the Provisional Application 60/162,897 filed Nov. 1, 1999, pursuant to 35 U.S.C. § 111(b).

TECHNICAL FIELD

The present invention relates to a process for efficiently obtaining a mixed gas of a lower olefin and a lower aliphatic carboxylic acid by gasifying a lower aliphatic carboxylic acid at a low temperature. The mixed gas obtained by this process is useful particularly in the process for producing a lower aliphatic ester, where a corresponding lower aliphatic ester is obtained from a lower olefin and a lower aliphatic carboxylic acid in a gas phase in the presence of an acidic catalyst. By virtue of this, a production process of a lower aliphatic ester, having excellent effect on the energy cost, can be provided.

BACKGROUND ART

A method of obtaining a corresponding lower aliphatic ester by reacting a lower olefin and a lower aliphatic carboxylic acid in a gas phase in the presence of an acidic catalyst such as a heteropolyacid has been heretofore known. Specific examples include those described in Japanese Unexamined Patent Publications No. 4-139149, No. 5-170699, No. 5-294894 and No. 9-118647. These production processes are methods of reacting a lower olefin and a lower aliphatic carboxylic acid by passing them over an acidic catalyst in a gas phase.

Among these, the catalysts described in Japanese Unexamined Patent Publications No. 5-294894 and No. 9-118647 are so-called supported catalysts in which a heteropolyacid and/or a heteropolyacid salt as the catalytically effective component is supported on a porous substance so as to increase the catalytic activity. However, in a gas-phase reaction using a supported catalyst comprising an acid catalyst such as heteropolyacid supported on a solid catalyst, when the reaction mixture in a liquid droplet form, namely, in a mist state is contacted with the solid catalyst, the catalytic component may flow out from the support. As a result, there arises a risk that the catalyst is deactivated within a short time or the catalytic component is mixed in the product and causes an unpredictable side reaction.

In order to avoid such a risk and stably perform the reaction over a long period of time, a raw material compound which is liquid at an ordinary temperature must be completely gasified during the reaction using the catalyst. The same applies to the production process of a lower aliphatic ester, where a corresponding lower aliphatic ester is obtained from a lower olefin and a lower aliphatic carboxylic acid in a gas phase in the presence of an acidic catalyst.

In this reaction, the excess use of a lower olefin is advantageous in view of the conversion of the lower aliphatic carboxylic acid and, therefore, the lower olefin is usually used in excess. Accordingly, it is essential in industry to recycle the lower olefin used in excess.

The pressure during the reaction is preferably higher because this is advantageous in view of the addition reaction and, therefore, a pressure as high as possible is suitably used. In this case, it is easily understood that a process performed while maintaining the entire reaction system including the above-described recycling system of the lower olefin at a high pressure (hereinafter simply referred to a "reaction process under pressure") is preferred.

As already described above, the lower aliphatic carboxylic acid introduced into the reaction system must be gasified so as to avoid a risk that the effective component flows out from the catalyst. In the reaction process under pressure, the gasified lower aliphatic carboxylic acid which is generated must have a pressure at least equal to, or higher than, the pressure within the system.

However, the lower aliphatic carboxylic acid generally has a large heat of vaporization and a large amount of energy is required to completely gasify it. Under high pressure, the heat of vaporization necessary for gasifying the lower aliphatic carboxylic acid is even larger. Thus, the reaction process under pressure causes a problem that a very large amount of energy is required.

On the other hand, the lower aliphatic carboxylic acid cannot attain a conversion of 100% in the above-described reaction even if a large excess of the lower olefin is used. Therefore, the process is usually designed to also recycle the unreacted lower aliphatic carboxylic acid.

However, the unreacted lower aliphatic carboxylic acid contains undesired by-products, in many cases. Specific examples of the undesired by-product include hydrocarbon compounds derived from the lower olefin, and carboxylic acid esters resulting from the reaction between the hydrocarbon compounds and the lower aliphatic carboxylic acid.

These by-products are generally unstable at high temperatures and, when the vaporizer is set to a high temperature to obtain a high-pressure gaseous low aliphatic carboxylic acid necessary for the reaction process under pressure, the by-products are decomposed by the heat and may cause a fouling of the vaporizer. Furthermore, when the starting material lower carboxylic acid has corrosiveness, such as formic acid and acetic acid, the corrosiveness is intensified under high pressure and high temperature and, thus, corrosion of the vaporizer arises as a problem.

Further, in the case where the lower aliphatic carboxylic acid has polymerizability, such as acrylic acid or methacrylic acid, exposure, per se, of the acid to a high temperature is undesirable.

As described above, the production process of a lower aliphatic ester, where a corresponding lower aliphatic ester is produced from a lower olefin and a lower carboxylic acid in a gas phase in the presence of an acidic catalyst, is expected to encounter problems such as deactivation of the catalyst resulting from the catalytic component flowing out from the supporter when the reaction mixture in a liquid droplet form, namely, in a mist state, contacts the solid catalyst, or reduction in the reaction results due to unpredictable side reactions caused by the inclusion of the catalytic components in the product.

In order to avoid such a risk and stably perform the reaction over a long period of time, the raw material compound which is liquid at an ordinary temperature must be completely gasified at the reaction using the catalyst. However, to elevate the temperature of the vaporizer of the low aliphatic carboxylic acid for attaining the complete gasification is not preferred not only from the point of view of energy cost but also in view of the side reaction due to the presence of impurities in the recycled lower aliphatic carboxylic acid or of the stability of the highly reactive lower aliphatic carboxylic acid itself.

These problems have, however, not been studied in conventional techniques.

DISCLOSURE OF INVENTION

It is an object of the present invention to provide a process for efficiently obtaining a mixed gas of a lower olefin and a lower aliphatic carboxylic acid by gasifying a lower aliphatic carboxylic acid, which is generally difficult to gasify because of its high boiling point and large heat of vaporization, at a relatively low temperature.

It is another object of the present invention to provide a process for producing a lower aliphatic ester, wherein a corresponding lower aliphatic ester is produced from a lower olefin and a lower carboxylic acid in a gas phase in the presence of an acidic catalyst such as a heteropolyacid, which has a particularly excellent effect on energy cost.

In order to attain the above-described objects, the present inventors have made extensive studies particularly on the method for efficiently gasifying a lower aliphatic carboxylic acid and, in turn, on the method for efficiently obtaining a mixed gas of a lower olefin and a lower aliphatic carboxylic acid, in the production process of a lower aliphatic ester where a lower aliphatic ester is produced from a lower olefin and a lower carboxylic acid in a gas phase in the presence of an acidic catalyst.

As a result, it has been found that when a lower aliphatic carboxylic acid is mixed with a lower olefin under an increased pressure and then gasified after heating, the temperature necessary for the gasification of the lower aliphatic carboxylic acid can be greatly reduced and thereby a mixed gas of a lower olefin and a lower aliphatic carboxylic acid can be efficiently obtained. The present invention has been accomplished based on this finding.

More specifically, the present invention provides a process for efficiently producing a mixed gas of a lower olefin and a lower aliphatic carboxylic acid, comprising mixing a lower aliphatic carboxylic acid with a lower olefin under increased pressure and then gasifying the mixture after heating.

The present invention also provides a process, for producing a lower aliphatic ester, comprising reacting a mixed gas of a lower olefin and a lower aliphatic carboxylic acid, obtained by the above-mentioned process of the present invention, in a gas phase in the presence of an acidic catalyst.

BEST MODE FOR CARRYING OUT THE INVENTION

Figure 1:
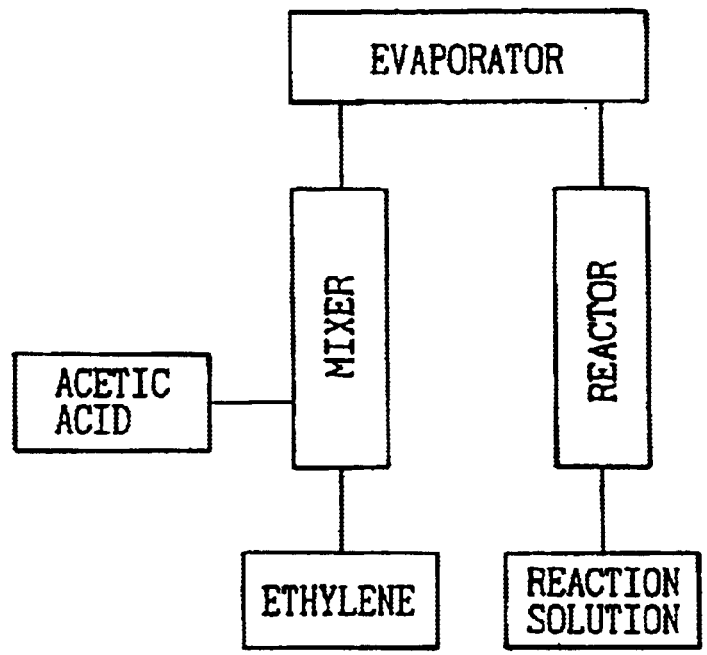
FIG. 1 is a flow sheet showing an embodiment of the present invention.

The lower olefin and the lower carboxylic acid used in the present invention as starting materials may each be either a material recycled by the reaction system or a purification system or a fresh material.

Where a lower carboxylic acid is gasified alone for feeding to a reaction process under pressure, the vaporizer must be operated under a pressure equal to or greater than the pressure in the reaction system and at a temperature higher than the boiling point of the lower carboxylic acid. However, according to the above-mentioned first process of the present invention, since the lower carboxylic acid is mixed with the lower olefin previously fed in a gas state, a necessary amount of lower carboxylic acid can be gasified by operating the vaporizer at a temperature where the partial pressure of the lower carboxylic acid required as a feed composition based on the total pressure in the reaction system becomes equal to the vapor pressure of the lower carboxylic acid.

In the reaction process under pressure, for improving the conversion of the lower carboxylic acid, the lower olefin starting material is desirably used at least in an equimolar amount to the carboxylic acid starting material, preferably in an excess amount of 2molar times or more, more preferably 10 molar times or more.

In this case, since the vapor pressure of the lower carboxylic acid becomes from a half to a few tenths of the total pressure in the reaction system, the temperature for gasifying the lower carboxylic acid can be greatly lowered.

The material of the vaporizer may be optionally selected from commonly used stainless steels such as SAS304, 316 and 316L, hastelloy-C, hastelloy-D and titanium, by taking account of the corrosiveness of the lower carboxylic acid at the temperature and pressure for gasifying the lower carboxylic acid, and the time period of continuously operating the vaporizer.

The vaporizer used for gasifying the starting material may be optionally selected from those such as of jacket type, natural circulation type, forced circulation type, coil type, plate type, falling thin film type, ascending film type, flash evaporation type and centrifugation type, according to the heating medium used, the operation conditions and the scale. However, in view of the thermal stability of the starting material carboxylic acid or for preventing the liquid lower carboxylic acid and water from splashing and accompanying the gas into the reactor, a natural circulation type evaporator, a falling thin film type evaporator and an ascending film type evaporator are generally preferred. For preventing the splashing and movement of the liquid materials, it is preferred to dispose a demister in the upper part of the evaporator or to make the liquid raw material lower aliphatic carboxylic acid fall from the upper part of the evaporator to absorb water and the liquid lower aliphatic carboxylic acid.

In the reaction process under pressure, since the reaction is a gas-phase addition reaction, the temperature and the pressure for the vaporization are preferably a high temperature and a high pressure. The temperature varies depending on the starting material used because the fed raw material must be kept in the gaseous state. Furthermore, in view of the balance with the energy cost, the temperature for the evaporation in general is preferably from 50 to 250° C., more preferably from 120 to 220° C., and the pressure is preferably from 0.2 to 3 MPa, more preferably from 0.2 to 1 MPa.

The acidic catalyst for use in the above-mentioned second process of the present invention may preferably a solid catalyst containing at least one acid point.

The solid catalyst containing at least one acid point may be an ordinary solid acid catalyst, and, for efficiently performing the addition of the lower aliphatic carboxylic acid to the lower olefin, those having many Broensted acid points are preferred. Examples of such an acid catalyst include heteropolyacids and salts thereof, supported catalysts obtained by causing a heteropolyacid, a salt thereof, or a mineral acid such as sulfuric acid or phosphoric acid to be supported on an appropriate support, ion exchange resins having a free sulfonic acid, and zeolites having an aluminosilicate skeleton.

The heteropolyacids comprise, for example, a center element and one or more peripheral elements bonded with oxygen. The center element is usually silicon or phosphorus but may comprise any one of various atoms belonging to Groups I to VIII of the periodic table of elements. Examples thereof include cupric ion: divalent beryllium, zinc, cobalt and nickel ions; trivalent boron, aluminum, gallium, iron, cerium, arsenite, phosphorus, bismuth, chromium and rhodium ions; tetravalent silicon, germanium, tin, titanium, zirconium, vanadium, sulfur, tellurium, manganese, nickel, platinum, thorium, hafnium, cerium and other rare earth ions; pentavalent phosphorus, arsenite, vanadium and antimony ions; hexavalent tellurium ion; and heptavalent iodide ion. Examples of the peripheral elements include tungsten, molybdenum, vanadium, niobium, tantalum and other metals. These heteropolyacids are also called "polyoxoanion", "polyoxometal salt" or "metal oxide cluster". Some structures of the anions are named in connection with the researchers in this field, for example, known as Kegin, Wels-Dorthon or Anderson-Evans-Pearoff structure. The heteropolyacids include not only monomers having a large molecular weight but also dimer complexes.

The heteropolyacids which can be used as the catalyst in the present invention is not particularly limited and specific examples of preferred heteropolyacids include:

tungstosilicic acid $H_4[SiW_{12}O_{40}]\cdot xH_2O$ tungstophosphoric acid $H_3[PW_{12}O_{40}]\cdot xH_2O$ phosphomolybdic acid $H_3[PMo_{12}O_{40}]\cdot xH_2O$ silicomolybdic acid $H_4[SiMo_{12}O_{40}]\cdot xH_2O$ phosphovanadomolybdic acid $H_{3+n}[PV_nMo_{12-n}O_{40}]\cdot xH_2O$ In addition, neutral salts of these heteropolyacids, such as lithium salts, potassium salts, cesium salts, rubidium salts, thallium salts, ammonium salts, copper salts, magnesium salts and gallium salts may be used.

The heteropolyacids may be used by forming them into a spherical form, a cylindrically extruded form, a granule, a pellet, a grain or a tablet.

In addition, a supported catalyst obtained by causing a heteropolyacid catalyst as described above, sulfuric acid, phosphoric acid or the like to be supported on a support may also be used as the catalyst. Examples of the support which can be used include inorganic supports such as silica, titania, silica-alumina, and alumina, and organic supports such as activated carbon and appropriately formed polymer.

As the ion exchange resin, ion exchange resins obtained by copolymerizing a sulfonic acid having a double bond, such as vinylbenzenesulfonic acid, with styrene and divinylbenzene may be used.

As the zeolite, H-type alminosilicates may be used, and those having an MFI skeleton are particularly preferred because of their acid strength.

The gas-phase reaction may be carried out either in a fixed bed system or a fluidized bed system. The shape of the support may be selected from powder to those formed into a size of a few mm according to the reaction system employed.

Examples of the starting material lower olefin include ethylene, propylene, 1-butene, 2-butene and isobutene. Examples of the lower aliphatic carboxylic acid include formic acid, acetic acid, propionic acid, n-butyric acid, isobutyric acid, acrylic acid and methacrylic acid.

With respect to the ratio of the raw materials used and passed on the acid catalyst, the lower olefin is preferably used in an equimolar amount, or in excess, with respect to the lower aliphatic carboxylic acid. More specifically, the molar ratio of the lower-olefin to the lower aliphatic carboxylic acid is preferably from 1:1 to 30:1, more preferably from 5:1 to 20:1.

In view of the life of the catalyst, a slight amount of water is preferably mixed with the raw material, but by-products of alcohol and ethers corresponding to the starting material lower olefin used, such as ethanol and diethyl ether corresponding to ethylene, are increased as the amount of water mixed is increased. Therefore, the amount of water used is preferably from 1 to 15 mol %, more preferably from 3 to 8 mol %, based on the total amount of the lower aliphatic carboxylic acid, the lower olefin and water used.

With respect to the space velocity (hereinafter referred to as "GHSV") of the starting material supplied to the catalyst, when the reaction is carried out without varying the reactor conditions and the amount of the catalyst amount is constant, the amount of carboxylic acid produced generally increases as the GHSV is elevated to a certain degree. However, if the GHSV is excessively elevated, the increasing rate of the amount of carboxylic acid ester produced decreases and the raw material conversion is also reduced. Furthermore, by elevating the GHSV, the pressure loss in the reaction system increases. Particularly in the case of a circulating system, the capacity required for the compressor of circulating the gas in an amount necessary for elevating the pressure in compensation for the pressure loss and attaining a predetermined GHSV disadvantageously increases. Therefore, the optimal GHSV must be selected according to the dependency of the reaction on the GHSV. The raw material is generally passed over the catalyst suitably at a GHSV of from 100 to 5,000 $hr^{-1}$, preferably from 300 to 2,000 $hr^{-1}$.

Furthermore, the alcohol or ether corresponding to the starting material lower olefin, generated by the reaction, may be recycled as it is together with the olefin or may be separated at a purification step and then recycled to the reactor.

The present invention is further illustrated below by referring to the Examples and Comparative Examples.

APPARATUS USED IN EXPERIMENTS

Figure 2:
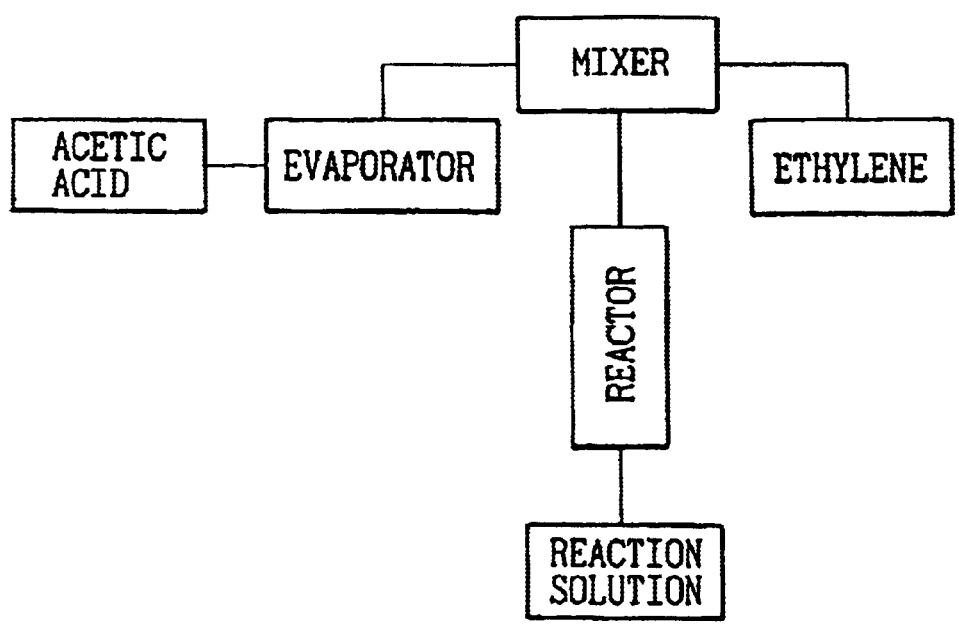
FIG. 2 is a flow sheet showing a conventional process.

The apparatus used in Examples had a structure shown in FIG. 1 and the apparatus used in Comparative Examples had a structure shown in FIG. 2. The reactor and the evaporator were common between Examples and Comparative Examples. The reactor was a vertical tube reactor having an inner diameter of 21.4 mm and an effective catalyst charging length of 325 mm. The evaporator used was composed of a stainless steel-made duplex tube and, in the inside tube having an inner diameter of 21.4 mm and a length of 400 mm, 100 $cm^3$ of glass beads having an outer diameter of 2 mm were packed. In the outside tube, an oil bath heated to a predetermined temperature was circulated and the acetic acid fed as a starting material was vaporized.

EXAMPLE 1

Catalyst

The catalyst used in this Example was a tablet-shaped catalyst comprising a cesium salt of tungstophosphoric acid and having a diameter of 5 mm. This catalyst was prepared as follows. In 300 ml-volume flask, 150 g (about 0.0438 mol) of a commercially available tungstophosphoric acid reagent (produced by Wako Junyaku K.K.) was mixed and dissolved in 60 ml of pure water. Separately, 21.5 g (0.110 mol) of cesium nitrate ($CsNO_3$) was dissolved in water and the resulting solution was added dropwise to the aqueous tungstophosphoric acid solution prepared above, using a dropping funnel while stirring. The moment the solution was added dropwise, white fine crystals of phosphowolframate (tungstophosphoric acid cesium salt) were precipitated. The flask was dipped in a water bath to vaporize the water content and the residual lump was transferred to a Petri dish, placed in a dryer and dried in air at 150° C. for 6 hours. The dried product was pulverized and formed into tablets having a diameter of 5 mm using a tablet machine.

Using the reactor shown in FIG. 1, ethylene, nitrogen, acetic acid and water were fed in a molar ratio of 80.0:10.3:6.7:3.0 from the respective inlets at a space velocity of 1,500 hr$^{-1}$ under a pressure of 0.9 MPa. Nitrogen was fed together with ethylene and water was fed together with acetic acid. In this case, the temperature at which the acetic acid-water mixture vaporized was 92.4° C. When the reaction system was heated so that the catalyst layer had a peak temperature of 165° C., the reaction results were such that the space time yield STY of ethyl acetate was 200 g/l·cat·h and the selectivities of ethyl acetate, ethanol and diethyl ether were 93.0%, 3.4% and 3.0%, respectively.

EXAMPLE 2

The catalyst used was the same as that used in Example 1.

Using the reactor shown in FIG. 1, ethylene, acetic acid and water were fed in a molar ratio of 87.0:5.0:8.0 from the respective inlets at a space velocity of 1,500 hr$^{-1}$ under a pressure of 0.9 MPa. Water was fed together with acetic acid. In this case, the temperature at which the acetic acid-water mixture vaporized was 102.3° C. When the reaction system was heated so that the catalyst layer had a peak temperature of 165° C., the reaction results were such that the STY of ethyl acetate was 176 g/l·cat·h and the selectivities of ethyl acetate, ethanol and diethyl ether were 91.5%, 4.3% and 3.7%, respectively.

EXAMPLE 3

The catalyst used was the same as used in Example 1.

Using the reactor shown in FIG. 1, propylene, nitrogen, acetic acid and water were fed in a molar ratio of 80.0:10.3:6.7:3.0 from the respective inlets at a space velocity of 1,500 hr$^{-1}$ under a pressure of 0.9 MPa. Nitrogen was fed together with propylene and water was fed together with acetic acid. In this case, the temperature at which the acetic acid-water mixture vaporized was 105.6° C. When the reaction system was heated so that the catalyst layer had a peak temperature of 165° C., the reaction results were such that the STY of isopropyl acetate was 243 g/l·cat·h and the selectivities of isopropyl acetate, isopropanol and diisopropyl ether were 94.7%, 2.8%, and 2.3%, respectively.

EXAMPLE 4

The catalyst used was the same as used in Example 1.

Using the reactor shown in FIG. 1, ethylene, nitrogen, acrylic acid and water were fed in a molar ratio of 80.0:10.3:6.7:3.0 from the respective inlets at a space velocity of 1,500 hr$^{-1}$ under a pressure of 0.3 MPa. Nitrogen was fed together with ethylene and water was fed together with acrylic acid. In this case, the temperature at which the acrylic acid-water mixture vaporized was 85.6° C. when the reaction system was heated so that the catalyst layer had a peak temperature of 165° C., the reaction results were such that the STY of ethyl acrylate was 52 g/l·cat·h and the selectivities of ethyl acrylate, ethanol and diethyl ether were 91.8%, 4.3% and 3.5%, respectively.

EXAMPLE 5

The catalyst used was a catalyst obtained by allowing a lithium salt of tungstophosphoric acid to be supported on a silica support (produced by Sudchemie GmbH) having a diameter of 5 mm. This catalyst was prepared as follows.

The support was dried in a hot air dryer at 110° C. for 4 hours to have a residual water content of 7% or less. In a 500 ml-volume flask, 298 g (about 0.104 mol) of a commercially available tungstophosphoric acid reagent-(produced by Wako Junyaku K.K.) was mixed and dissolved under heating in 120 ml of pure water. Separately, 0.076 g (0.0011 mol) of lithium nitrate (LiNO$_3$) was dissolved in pure water and the resulting solution was added dropwise to the aqueous tungstophosphoric acid solution prepared above, using a dropping funnel while stirring. The stirring was continued at room temperature for 30 minutes to obtain a uniform solution and, to the resulting solution, pure water was added until the volume reached 95% of the saturated liquid absorption amount of the supporter, thereby forming an impregnating solution. To this impregnating solution, 1 L of the support was added, and then the solution was thoroughly stirred to completely impregnate the support and thereby allow the catalyst to be uniformly supported. The resulting impregnated product was air dried for 1 hour and then dried in a hot air dryer at 150° C. for 5 hours to obtain a supported catalyst.

The thus-obtained catalyst was filled in the reactor shown in FIG. 1 and, thereto, ethylene, nitrogen, acetic acid and water were fed in a molar ratio of 78.5:9.0:8.0:4.5 from the respective inlets at a space velocity of 1,500 hr$^{-1}$ under a pressure of 0.9 MPa. Nitrogen was fed together with ethylene and water was fed together with acetic acid. In this case, the temperature at which the acetic acid-water mixture vaporized was 102.2° C. When the reaction system was heated so that the catalyst layer had a peak temperature of 165° C., the reaction results were such that the space time yield STY of ethyl acetate was 215 g/l·cat·h and the selectivities of ethyl acetate, ethanol and diethyl ether were 90.8%, 5.0% and 4.2%, respectively.

EXAMPLE 6

A catalyst was prepared in the same manner as in the catalyst preparation procedure in Example 5, except that 0.007 g (0.0001 mol) of lithium nitrate was used.

The thus-obtained catalyst was filled in the reactor shown in FIG. 1 and, thereto, ethylene, nitrogen, acetic acid and water were fed in a molar ratio of 78.5:9.0:8.0:4.5 from the respective inlets at a space velocity of 1,500 hr$^{-1}$ under a pressure of 0.9 MPa. Nitrogen was fed together with ethylene and water was fed together with acetic acid. In this case, the temperature at which the acetic acid-water mixture vaporized was 102.2° C. When the reaction system was heated so that the catalyst layer had a peak temperature of 165° C., the reaction results were such that the space time yield STY of ethyl acetate was 174 g/l·cat·h and the selectivities of ethyl acetate, ethanol and diethyl ether were 92.1%, 5.7% and 2.2%, respectively.

EXAMPLE 7

A catalyst was prepared in the same manner as in the catalyst preparation procedure in Example 5, except that 345 g (0.120 mol) of tungstosilicic acid and 0.083 g (0.120 mol) of lithium nitrate were used.

The thus-obtained catalyst was filled in the reactor shown in FIG. 1 and, thereto, ethylene, nitrogen, acetic acid and water were fed in a molar ratio of 78.5:9.0:8.0:4.5 from the respective inlets at a space velocity of 1,500 hr$^{-1}$ under a pressure of 0.9 MPa. Nitrogen was fed together with ethylene and water was fed together with acetic acid. In this case, the temperature at which the acetic acid-water mixture vaporized was 102.2° C. when the reaction system was heated so that the catalyst layer had a peak temperature of 165° C., the reaction results were such that the space time yield STY of ethyl acetate was 254 g/l-cat·h and the selectivities of ethyl acetate, ethanol and diethyl ether were 87.7%, 7.6% and 4.7%, respectively.

EXAMPLE 8

A catalyst was prepared in the same manner as in the catalyst preparation procedure in Example 5, except that 541 g (0.194 mol) of tungstophosphoric acid was used instead of 298 g of tungstophosphoric acid and 1.323 g (0.0012 mol) of lithium nitrate was used instead of 0.076 g.

The thus-obtained catalyst was filled in the reactor shown in FIG. 1 and thereto, ethylene, nitrogen, acetic acid and water were fed in a molar ratio of 78.5:9.0:8.0:4.5 from the respective inlets at a space velocity of 1,500 hr$^{-1}$ under a pressure of 0.9 MPa. Nitrogen was fed together with ethylene and water was fed together with acetic acid. In this case, the temperature at which the acetic acid-water mixture vaporized was 102.2° C. When the reaction system was heated so that the catalyst layer had a peak temperature of 165° C., the reaction results were such that the space time yield STY of ethyl acetate was 196 g/l-cat·h and the selectivities of ethyl acetate, ethanol and diethyl ether were 90.1%, 6.6% and 3.3%, respectively.

COMPARATIVE EXAMPLE 1

The catalyst used was the same as used in Example 1.

Using the reactor shown in FIG. 2, ethylene, nitrogen, acetic acid and water were fed in a molar ratio of 80.0:10.3:6.7:3.0 from the respective inlets at a space velocity of 1,500 hr$^{-1}$ under a pressure of 0.9 MPa. Nitrogen was fed together with ethylene and water was fed together with acetic acid. When the temperature of the evaporator was set to be the same as in Example 1 (92.4° C.), the acetic acid-water mixture did not vaporize and only ethylene was fed to the reactor. As a result, a polymerization reaction of ethylene occurred on the catalyst in the reactor and the catalyst was deactivated.

Then, the temperature of the evaporator was elevated to a temperature where the acetic acid-water mixture vaporized, and the temperature was 194.4° C. When the peak temperature of the catalyst layer was 165° C., the reaction results were such that the STY of ethyl acetate was 198 g/l-cat·h and the selectivities of ethyl acetate, ethanol and diethyl ether were 92.7%, 3.6% and 3.2%, respectively.

COMPARATIVE EXAMPLE 2

The catalyst used was the same as that used in Example 1.

Using the reactor shown in FIG. 2, ethylene, nitrogen, acrylic acid and water were fed in a molar ratio of 80.0:10.3:6.7:3.0 from respective inlets at a space velocity of 1,500 hr$^{-1}$ under a pressure of 0.3 MPa. Nitrogen was fed together with ethylene and water was fed together with acrylic acid. When the temperature of the evaporator was set to be the same as in Example 4 (85.6° C.), the acrylic acid-water mixture did not vaporize and only ethylene was fed to the reactor. As a result, a polymerization reaction of ethylene occurred on the catalyst in the reactor and the catalyst was deactivated.

Then, the temperature of the evaporator was elevated to a temperature where the acrylic acid-water mixture vaporized, and the temperature was 163.8° C. When the vaporization was performed at this temperature; fouling took place in the evaporator due to the polymerization of acrylic acid. As a result, the acrylic acid-water mixture could not be gasified in the evaporator and only ethylene was fed to the reactor. Then, the catalyst was deactivated due to the polymerization of ethylene within the reactor.

INDUSTRIAL APPLICABILITY

As described above, by mixing a lower aliphatic carboxylic acid with a lower olefin under an increased pressure and then gasifying it after heating, the temperature of gasification of the lower aliphatic carboxylic acid can be greatly reduced, so that a mixed gas of a lower olefin and a lower aliphatic carboxylic acid can be effectively obtained. As a result, the energy cost necessary for the gasification can be reduced and, due to the improved stability of the gasifying solution, the vaporizer can be safely operated.

What is claimed is:

1. A process for producing a mixed gas of a lower olefin and a lower aliphatic carboxylic acid, comprising mixing a lower olefin having 1 to 4 carbon atoms and a lower aliphatic carboxylic acid having 1 to 4 carbon atoms under pressure, and subsequently heating to gasify the mixture.

2. The process as claimed in claim 1, wherein the pressure at the mixing is from 0.2 to 2 MPa.

3. The process as claimed in claim 1 or 2, wherein the temperature at gasification is from 50 to 250° C.

4. The process as claimed in claim 1 or 2, wherein the lower olefin is at least one member selected from the group consisting of ethylene, propylene, 1-butene, 2-butene, isobutene and butadiene.

5. The process as claimed in claim 1 or 2, wherein the lower aliphatic carboxylic acid is at least one member selected from the group consisting of formic acid, acetic acid, propionic acid, n-butyric acid, iso-butyric acid, acrylic acid and methacrylic acid.

6. A process for producing a lower aliphatic carboxylic acid ester having 1 to 4 carbon atoms in each ailkyl group comprising reacting, in a gas phase, a mixed gas of a lower olefin having 1 to 4 carbon atoms and a lower aliphatic carboxylic acid having 1 to 4 carbon atoms obtained by the process described in claim 1 or 2 in the presence of a solid acidic catalyst which is a heteropolyacid or a salt thereof.

7. The process as claimed in claim 6, wherein the heteropolyacid or a salt thereof is supported on a support.

8. The process as claimed in claim 6, wherein the reaction is performed in the presence of gaseous water.

9. The process as claimed in claim 3, wherein the lower olefin is at least one member selected from the group consisting of ethylene, propylene, 1-butene, 2-butene, isobutene and butadiene.

10. The process as claimed in claim 3, wherein the lower aliphatic carboxylic acid is at least one member selected from the group consisting of formic acid, acetic acid, propionic acid, n-butyric acid, iso-butyric acid, acrylic acid and methacrylic acid.

11. The process as claimed in claim 4, wherein the lower aliphatic carboxylic acid is at least one member selected from the group consisting of formic acid, acetic acid, propionic acid, n-butyric acid, iso-butyric acid, acrylic acid and methacrylic acid.

12. The process as claimed in claim 8, wherein the mixture has a vaporization temperature of 105.6° C. or less.

* * * * *